United States Patent [19]
Durette

[11] Patent Number: 6,123,081
[45] Date of Patent: Sep. 26, 2000

[54] OCULAR SURGICAL PROTECTIVE SHIELD

[76] Inventor: Jean-Francois Durette, 1170 East Henri-Bourassa Blvd., Montreal, Quebec, Canada, H2C 1G4

[21] Appl. No.: 09/400,753

[22] Filed: Sep. 22, 1999

[51] Int. Cl.[7] .................................................. A61F 9/00
[52] U.S. Cl. .................................................. 128/858; 2/15
[58] Field of Search .................. 128/846, 857, 128/858; 2/11, 15

[56] References Cited

U.S. PATENT DOCUMENTS

| | | | |
|---|---|---|---|
| 3,068,863 | 12/1962 | Bowman | 128/858 |
| 4,570,626 | 2/1986 | Norris | 128/858 |
| 4,701,962 | 10/1987 | Simon | 128/858 |
| 5,368,590 | 11/1994 | Itoh | 128/858 |
| 5,487,394 | 1/1996 | Shiu | 2/15 |

*Primary Examiner*—Michael A. Brown
*Attorney, Agent, or Firm*—James C. Nemmers

[57] ABSTRACT

A protective shield shaped to fit either the right or left ocular globe and formed sufficiently large to provide maximum protection of the globe. The shield has a proper vault at the cornea to minimize corneal abrasion and is formed with a flattened area at the edge where the shield will be positioned at the trochlea which is the cartilaginous structure positioned nasally and superiorly relative to the globe. A similar flattened area may also be formed along the edge of the shield at the temporal side where there is a lateral canthal tendon. The shields may be made with a peg or handle positioned to be at the juncture of the lid closure over the globe.

12 Claims, 1 Drawing Sheet

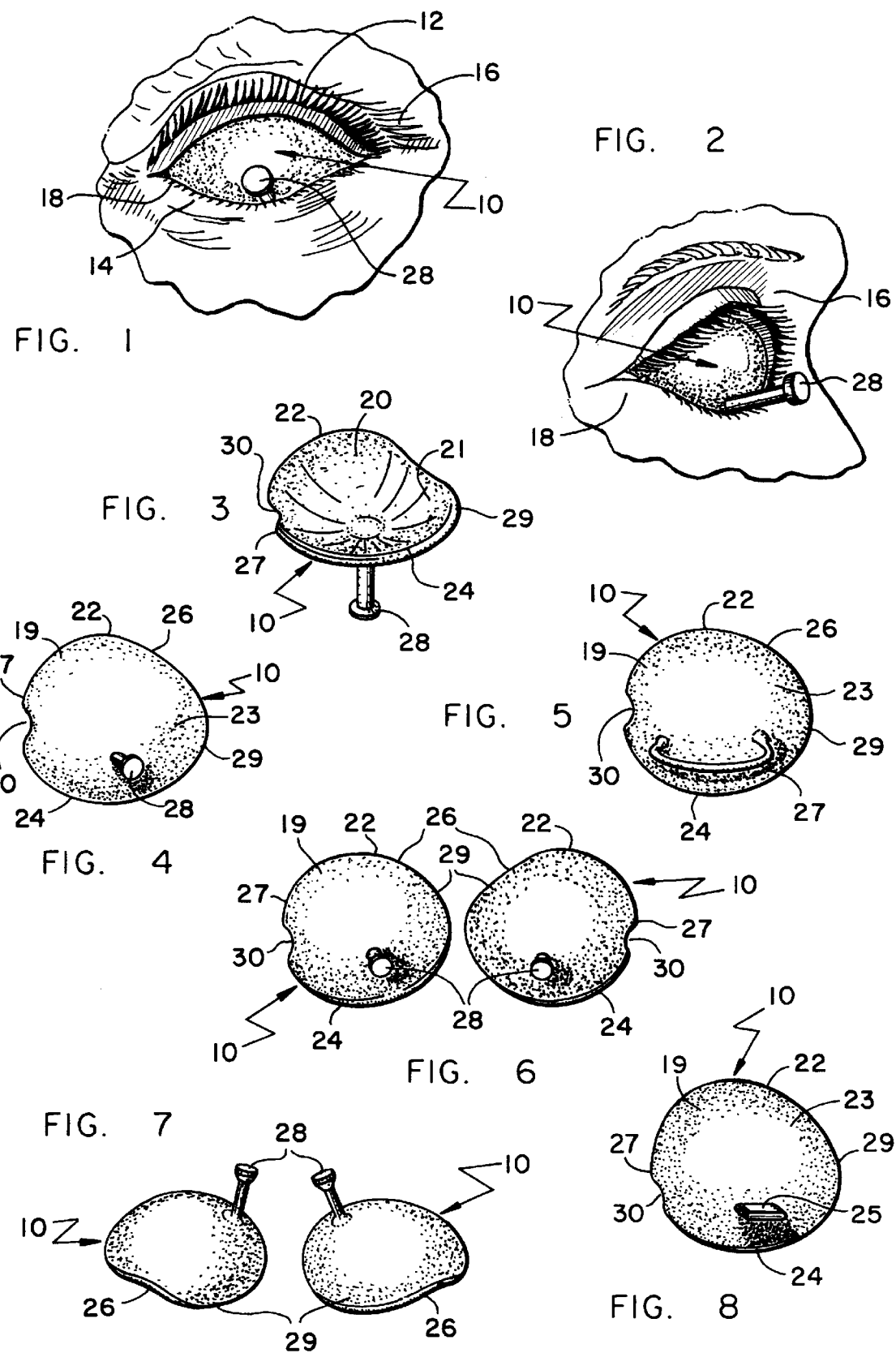

OCULAR SURGICAL PROTECTIVE SHIELD

BACKGROUND OF THE INVENTION

Ocular shields are commonly used to protect a patient's eyes during various surgical procedures where scalpels, electro-cauterizers or lasers are used to carry out the surgical procedures. Protection of the patient's eyes is extremely important during these various skin resurfacing or incisional procedures when they are performed on the head or neck of a patient.

To protect the patient's eyes, a variety of shields are known and used and are designed to conform to the ocular globe with a vault over the cornea. These shields are inserted behind the lids and over the patient's eyes after application of a topical anesthetic and an ophthalmic ointment to aid in the comfort and safety of the patient. These shields must be of the proper size so as to cover the globe during the surgical procedure, especially during periorbital surgery.

Some of the presently known and used shields do incorporate a vault at the cornea to clear the area of the cornea, although some shields do not closely conform to the curvature of the globe and actually compress the cornea and may irritate it. Most of the shields currently used are interchangeable so that they will fit either globe and thus can be inserted on either side simply by inverting them. Some such shields are either round bilateral while others are shaped more elongated with a pointed area positioned nasally.

These shields that can be used on either globe require that the shields be somewhat smaller and thus do not provide complete protection for the globes. If a larger bilateral shield is used, it may hit structures surrounding the globe and be painful to wear. Such larger bilateral shields are also difficult to insert and remove.

Some shields are designed to be removed using a suction cup, while others have A gripping device, such as an integral peg or handle, to aid in the insertion and removal of the shields. Shields with a peg or handle have been used for a number of years, but the presently available shields position the peg at or near the center of the shield or at the temporal side. The shields that use handles are easier for the surgeon to remove, but in the case of either the peg or handle, they are positioned in the path of the normal movement of the upper lid. Thus, each time the upper lid closes, the handle or peg is struck by the upper lid which displaces the shield downward or may even rotate the shield rubbing it against the cornea and may occasionally cause corneal abrasion.

Depending upon the type of surgical procedure with which the ocular shields are used, they are made either of colored opaque or clear plastic or stainless steel. The plastic shields are typically used for procedures where the surgeon uses a scalpel or electrocauterizer while the metallic shields are used during surgical procedures using a laser. Most shields, whether plastic or metallic are autoclavable, although not all are.

None of the presently known ocular protective shields provide a shield large enough to protect as much as possible of the globe while still being easy to insert and remove and more comfortable for the patient. There is therefore a need for an improved shield that maximizes the protection, is easy for the surgeon to use, and which provides better comfort and less risk for the patient.

SUMMARY OF THE INVENTION

The ocular protective shields of the invention are shaped to fit either the right or left globe (i.e., not both sides) and formed sufficiently large and with a proper vault at the cornea to provide maximum protection of the globe while minimizing corneal abrasion. Each of the shields is formed with a notch (flattened area at the edge) where the shield will be positioned at the trochlea which is the cartilaginous structure positioned nasally and superiorally relative to the globe. A similar notch (flattened area at the edge) may also be formed at the temporal side where there is a lateral canthal tendon. This shield is longer superiorally than inferiorally and thus covers more of the globe. The shields may be made with a peg or handle positioned to be at the juncture of the lid closure. The shields may be provided without a peg or handle and removed with suction cups.

BRIEF DESCRIPTION OF THE DRAWING

FIG. 1 is a frontal view of an eye with the ocular shield of the invention fully inserted;

FIG. 2 is a side view of an eye with the ocular shield of the invention fully inserted;

FIG. 3 is a perspective view showing the curvature of the posterior side of the shield;

FIG. 4 is a front view of the shield of FIG. 3, being a shield for the right globe with a gripping peg in place;

FIG. 5 is a front view of a shield similar to FIG. 4 but showing the shield with a gripping wire handle in place;

FIG. 6 is a frontal view showing a pair of shields constructed according to the principles of the invention;

FIG. 7 is a perspective view of a pair of shields from a nasal view; and

FIG. 8 is a front view of a shield similar to FIG. 5 but showing the shield with a solid gripping handle in place.

DESCRIPTION OF THE PREFERRED EMBODIMENT OF THE INVENTION

The drawings illustrate the embodiment of the invention in which the ocular shield has formed integrally with it a gripping device, such as a peg, to aid in the insertion and removal of the shield. Referring first to FIG. 1, there is illustrated an ocular shield, indicated generally by the reference numeral 10, fully inserted and in place over the globe of a patient's eye. As is well known, the globe is covered by an upper eyelid 12 and a lower eyelid 14, and although not shown, near the ocular globe is positioned the trochlea which is a cartilaginous structure on the upper nasal side 16 of the globe. Opposite the nasal area of the ocular globe is the temporal side 18 where there is a lateral canthal tendon (not shown).

The shield 10 of the invention has a main body 19 that forms a vault 20 fit over the cornea, the curvature of the vault 20 being shaped to fit over the globe so as not to flatten the cornea and risk irritating it. The shield 10 has a back or posterior side 21 and a front or anterior side 23. The superior edge 22 of the shield 10 is longer than the inferior edge 24, and the shield 10 has a temporal end 27 and a nasal end 29. Preferably, the edges 22 and 24 are polished as is the surface of the posterior side 21. The anterior surface 19 may also be polished or made with a non-glare surface, depending upon the type of surgery with which the shield 10 will be used.

As shown in the drawings, the shields 10 are somewhat round in shape so as to cover and protect more of the ocular globe. However, in order to fit better, each of the ocular shields 10 is somewhat flattened or notched along the superior edge 22 near the nasal side 29 where the shield 10 will be positioned at the trochlea. This "notch" is shown by reference numeral 26.

As shown in the drawings, a similar notch 30 may be formed between the superior edge 22 and the inferior edge 24 at the temporal end 27. This temporal notch 30 is somewhat smaller than the notch 26 and would relief pressure of the shield when it presses against the lateral canthal tendon, especially for the shields 10 made in the larger sizes.

In the embodiments shown in the drawings, a gripping device, such as peg 28, is formed integrally with the shield 10. FIG. 5 shows the gripping device to be a wire handle 27, and FIG. 8 shows the gripping device as a solid, rectangular-shaped handle 25 that can be more easily molded with the main body 10. A simple post (not shown) may also be used. Unlike the prior art ocular shields, the peg 28, handle 27 or handle 25 is positioned 6 to 8 mm. lower than the apex of the shield 10 which is the summit of the shield on top of the cornea. The peg 28, handle 27 or handle 25 is preferably positioned at the downward position of the junction between the sclera and the cornea of the ocular globe, which is the normal anatomical place of junction of the closure of the upper eyelid 12 and lower eyelid 14. Since most corneas are 12 mm. in diameter and the lower lid is typically 1 or 2 mm. lower than the limbus, positioning the peg 28 6 to 8 mm. below the apex of the cornea positions it near or against the lower eyelid 14. Since the lower eyelid hardly moves upwardly, this enables the upper eyelid 12 to close without hardly engaging the peg 28 and moving the shield. This thus prevents any potential shifting downward or rotation of the shield 10 with resulting pressure on the cornea. This proper position is illustrated in FIGS. 1 and 2.

The shield of the invention can be made of plastic or stainless steel and in either case can be made to be autoclavable. Although some plastics are not autoclavable, all shields 10 should have their posterior side 21 and their edges 22 and 24 highly polished to avoid any corneal abrasions.

It should be understood that the shield of the invention in another embodiment can be made without the peg 28 or any other gripping device which would require the use of a suction cup for insertion and removal of the shield. Since the shields of the invention are contoured to fit more closely over the ocular globe, if difficulty is encountered in removing the shield, suction between the shield and the ocular globe can be decreased by providing the shield with a very small relief hole (1 mm. or less) slightly superiorally to the area of the cornea. The use of such a relief hole could only be used on plastic ocular shields and not on metal shields used to protect the globe during laser surgery since the hole would allow the laser to pass through and hit the globe.

Having thus described the invention in connection with the preferred embodiments thereof, it will be evident to those skilled in the art that various revisions can be made to the preferred embodiments described herein without departing from the spirit and scope of the invention. It is my intention, however, that all such revisions and modifications that are evident to those skilled in the art will be included within the scope of the following claims.

What is claimed is as follows:

1. An ocular shield for placement over the ocular globe, including the cornea, and under the upper and lower lids of the eye of a patient during a surgical procedure, said shield comprising: a relatively thin, curved main body that forms a vault the curvature of which is shaped to fit over the ocular globe so as not to flatten the cornea; the main body having a superior edge and an inferior edge joined at a nasal end and a temporal end, the superior edge being longer than the inferior edge; and a notch formed along the superior edge near the nasal end.

2. The ocular shield of claim 1 in which a notch is also formed at the juncture of the superior edge and the inferior edge at the temporal end of the main body.

3. The ocular shield of claim 2 in which a gripping device is combined with the main body to assist in inserting and removing the shield.

4. The ocular shield of claim 3 in which the gripping device is positioned on the main body so as to be near or against the lower lid of the patient's eye whether the lids are closed or opened.

5. The ocular shield of claim 1 in which a gripping device is combined with the main body to assist in inserting and removing the shield.

6. The ocular shield of claim 3 in which the gripping device is positioned on the main body so as to be near or against the lower lid of the patient's eye whether the lids are closed or open.

7. The ocular shield of claim 6 in which the curved main body has an apex, and the gripping device is positioned below the apex toward the inferior edge of the main body.

8. The ocular shield of claim 7 in which the gripping device is positioned 6 to 8 mm below the apex of the main body.

9. The ocular shield of claim 8 in which the gripping device is a peg extending outwardly from the main body.

10. The ocular shield of claim 8 in which the gripping device is a flat handle extending outwardly from the main body.

11. The ocular shield of claim 8 in which the gripping devices is a wire handle extending outwardly from the main body.

12. The ocular shield of claim 1 in which the edges and the posterior side of the main body are polished to a smooth surface.

* * * * *